United States Patent
Rosende Barturen

(10) Patent No.: US 9,255,869 B2
(45) Date of Patent: Feb. 9, 2016

(54) SOURCE, WHICH HARNESSES THE DIFFERENCE IN DENSITY BETWEEN FLUIDS FOR THE PRODUCTION OF RENEWABLE ENERGY

(71) Applicant: Francisco Javier Rosende Barturen, Madrid (ES)

(72) Inventor: Francisco Javier Rosende Barturen, Madrid (ES)

(73) Assignee: Francisco Javier Rosende Barturen, Madrid (ES)

( * ) Notice: Subject to any disclaimer, the term of this patent is extended or adjusted under 35 U.S.C. 154(b) by 0 days.

(21) Appl. No.: 14/664,031

(22) Filed: Mar. 20, 2015

(65) Prior Publication Data
US 2015/0293003 A1    Oct. 15, 2015

(30) Foreign Application Priority Data
Apr. 9, 2014    (ES) .................................. 201400300

(51) Int. Cl.
F03B 17/04    (2006.01)
F01K 27/00    (2006.01)
G01N 9/28    (2006.01)

(52) U.S. Cl.
CPC ........................ *G01N 9/28* (2013.01)

(58) Field of Classification Search
CPC ................................. F03B 17/04; F01K 27/00

USPC .................................................. 73/439
See application file for complete search history.

(56) References Cited

U.S. PATENT DOCUMENTS

2008/0303282 A1*    12/2008    Ziegenfuss ............ F03B 17/005
                                                                    290/52

FOREIGN PATENT DOCUMENTS

| ES | 2365074 A1 | 9/2011 | |
| WO | WO 0047891 A1 * | 8/2000 | ............ F03B 11/002 |
| WO | WO 03001057 A1 * | 1/2003 | .............. F03B 17/02 |
| WO | WO 2011110706 A1 * | 9/2011 | .............. F01K 27/00 |

* cited by examiner

*Primary Examiner* — Lisa Caputo
*Assistant Examiner* — Jamel Williams
(74) *Attorney, Agent, or Firm* — Foley & Lardner LLP; Sunit Talapatra

(57) ABSTRACT

The invention relates to the method of feeding the air, or fluid of lower density, into the duct (2) by means of tubes separated one from another in such a way that there should be water, or liquid fluid, between them, so that this bathes at least part of its walls. In other words, similar to the stalks of a bouquet submerged in water, and at whose ends, instead of flowers, air bubbles exit, these being produced at the air inlet at the extremity of the stalk or tube. It relates more specifically to the method of feeding the lower-density fluid by means of tubes which at their base are grouped, close to each other or touching, and at their outlet extremities are separated, as if forming a bouquet, in such a way that the separation distance of the extremities of the tubes, between axes of symmetry, is approximately the diameter of the bubble.

14 Claims, 14 Drawing Sheets

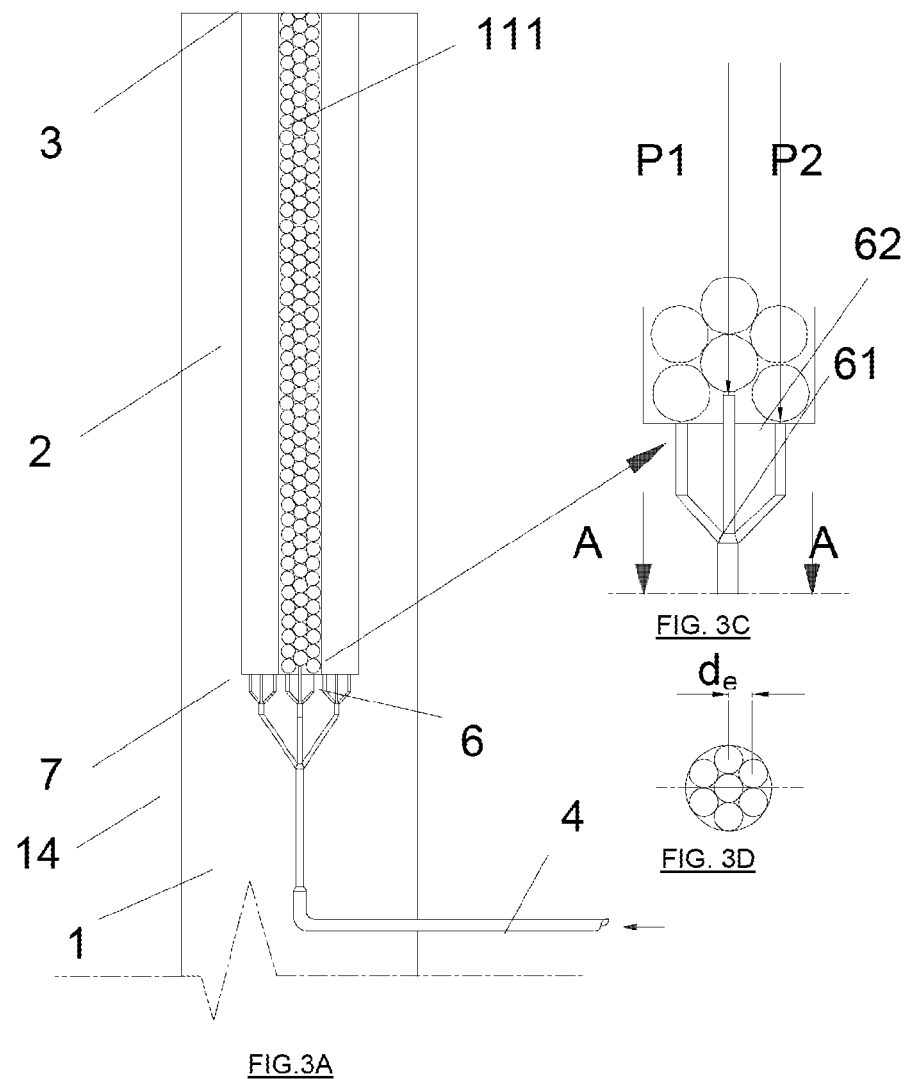
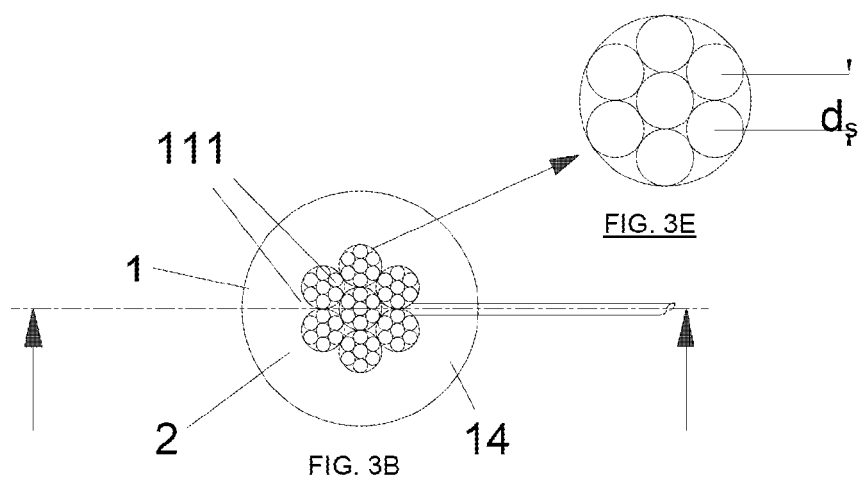

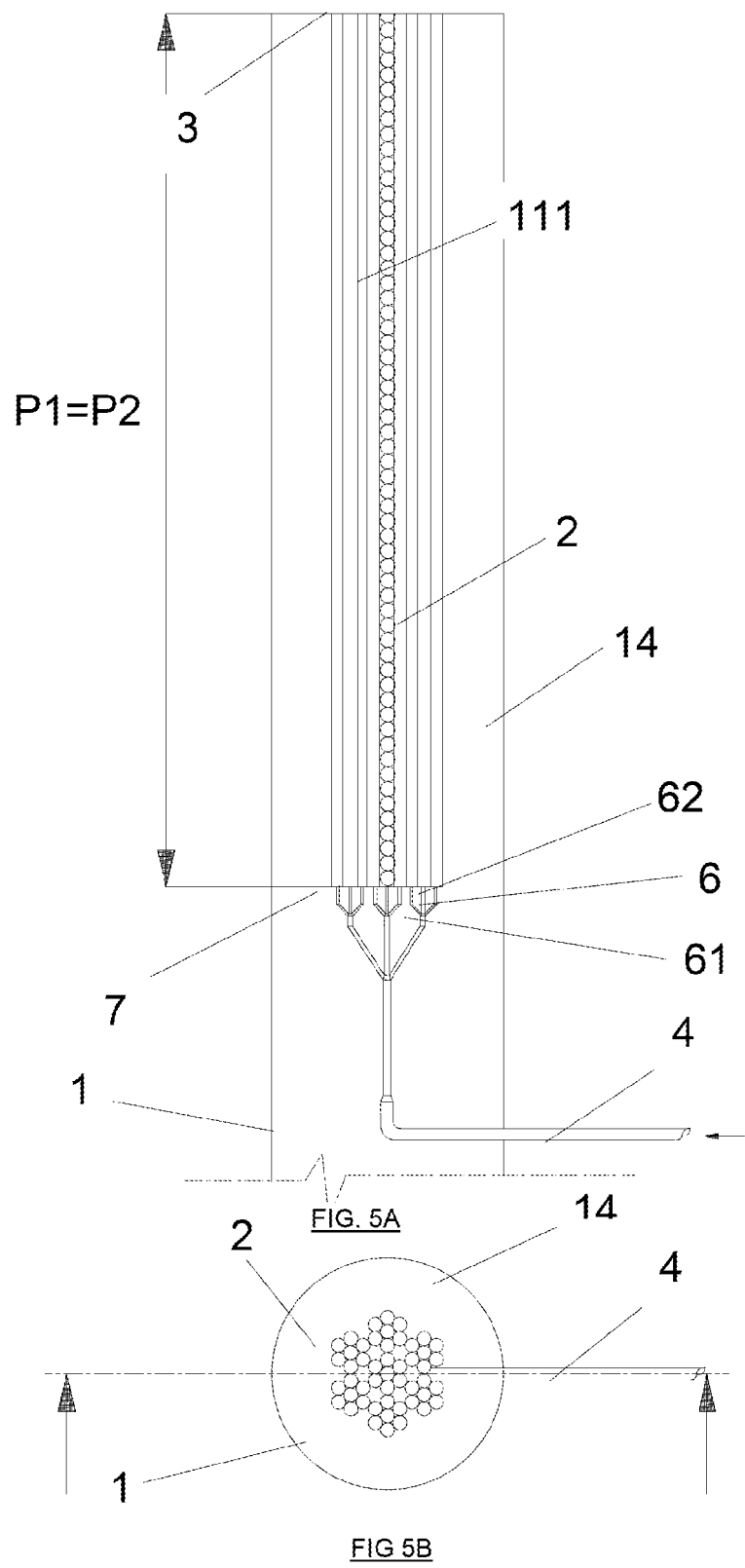

SOURCE, WHICH HARNESSES THE DIFFERENCE IN DENSITY BETWEEN FLUIDS FOR THE PRODUCTION OF RENEWABLE ENERGY

TECHNICAL FIELD OF THE INVENTION

The present invention relates to a series of improvements introduced in the Spanish patent No. P201000275 relating to a source which harnesses the difference in density between fluids for the production of renewable energy.

BACKGROUND OF THE INVENTION

Spanish patent P201000275 describes a source of renewable energy for the production of mechanical or electrical energy, comprising a duct submerged in a fluid, generally water, contained within another tube or vessel, whose outlet section is approximately at the same level as the free surface of the water, and its inlet at a lower level. The system likewise features an element which introduces a fluid of lower density, usually air, into the interior of this duct, by means of bubbles of uniform size, and preferably of relatively small size, approximately in the same direction as the duct and occupying the entirety of its profile, which brings about the upward mobility of said fluid (air-water mixture) towards the surface. The upward mobility is due to the hydrostatic upthrust exerted by the water outside the duct (greater density) from the lower section of the duct on the fluid (air-water mixture) located within the duct, this featuring a lower density. Thus, as in Archimedes' upthrust, the air bubbles borne by the water situated within the duct transmit part of their upthrust to the water. The energy of this induced flow is what is harnessed, as is the static and dynamic pressure of the fluid with the lower density, generally air, which is fed into the duct under static and dynamic pressure.

DESCRIPTION OF THE INVENTION

The invention relates to a generator comprising a distributor configured so as to introduce a second fluid of a second density, this second density being a lower density; this second fluid may be air; into a duct containing a first fluid of a first density, this first density being a higher density; this first fluid may be water. In the invention, when the second fluid of a second density, or fluid with lower density is mentioned, said fluid may be air, and when the first fluid of a first density, or fluid with higher density is mentioned, said fluid may be water. The distributor may be comprised of a plurality of tubes. The tubes feature a first extremity, configured so as to receive the ingress of a second fluid, of lower density, and a second extremity, configured so as to expel a second fluid, of lower density. The second extremities of the tube are connected to the duct. The tubes are arranged in the shape of a bouquet, each tube being a stalk of the bouquet; that is, the first extremities of the tube are close together, at an entry distance $d_e$ from each other, while the second extremities of the tube are more separated from each other, at an outlet distance $d_o$. The outlet distance $d_o$ is configured so that within the duct, between the second extremities, there shall be first fluid, of a higher density, covering at least part of the internal walls of the duct. That is to say that the arrangement of the distributor tubes is similar to the stalks of a bouquet and that instead of flowers, it features second extremities through which the second fluid exits, forming the bubbles of second fluid (air) in the first fluid (water). The second fluid emanates from a second fluid (air) entry point at the start of the stem of the bouquet.

At their base, the tubes may be grouped, close to each other or touching, and at their outlet extremities may be separate. The outlet distance $d_o$, determined by the separation between the axes of symmetry of the second extremities of the tubes, is approximately the diameter of the bubble. The tubes all feature the same internal diameter and the second fluid, of a lower density, which may be air, is at the same pressure in all the tubes; for this reason, the bubbles formed are of uniform size. As the distance between axes of symmetry is equal to, or slightly greater than, the diameter of the bubbles, the bubbles exit touching each other. By means of this arrangement, a greater sectional area of the second fluid, which may be air, is obtained versus that of the first fluid, which may be water, in order to obtain a proportion of second fluid, which may be air, greater than that of the first fluid, which may be water.

The distributor of the invention achieves the following:
That the proportion of second fluid, which may be air, is greater than that of first fluid, which may be water, within the duct with first fluid (water) and with bubbles of second fluid (air). This greater proportion of second fluid versus first fluid enables a considerable increase in the efficiency of the source of renewable energy.
A correct distribution of bubbles of second fluid (air) in the first fluid (water).
That the bubbles exit approximately in the direction of the duct, which enables the harnessing of the kinetic energy or dynamic pressure, also enabling the obtaining of high flowrates of second fluid (air) over the same profile of the duct.
Bubbles of uniform size, in order that the rising speed may be the same in all of them, thus avoiding collisions and the formation of larger-sized bubbles.
The selection of bubble size, this depending fundamentally on the internal profile of the tube and on the static and dynamic pressures.
The covering of the practical entirety of the transversal profile of the duct, with small spaces or interstices with first fluid, which may be water, among columns of bubbles of second fluid, which may be air.

A first embodiment of the distributor consists of a bouquet of tubes. A second embodiment of the distributor consists of a plurality of channels of first fluid at the inlet section in order to achieve improved distribution and bubble formation.

The obtaining of a high proportion of second fluid (lower density), which may be air (bubbles) within the first fluid (higher density), which may be water, is fundamental, as it increases profitability in all applications, as using the same quantity of energy for generator operation, the power and the efficiency of the process increase. In some applications this is essential or critical; if a high percentage of second fluid, which may be air (bubbles), is not obtained, the process will not be profitable, however much the length of the duct, through which the first fluid and second fluid flow, is increased (unless the outlet is maintained at negative pressure). In order to achieve a higher proportion of air versus water, or of the fluid with a lower density versus the fluid with a higher density; that is, second fluid versus first fluid, the entry of second fluid (air) is conducted thus:

By means of bouquets of tubes in such a way that their second extremities are separated by approximately the diameter of a bubble, in order to obtain the maximum outlet area of second fluid (air) versus the profile area of the first fluid (water) in a cross-section of the duct.

The second extremities of the tubes are located at different levels, so as to procure that the bubbles of second fluid, which may be air, touch each other according to a longitudinal axis of the duct, in order to obtain the maximum outlet area of first fluid, which may be water, on a transversal plane of the duct.

DESCRIPTION OF THE FIGURES

In order to complete the description made herein, and for the purpose of aiding the better understanding of the invention, a set of drawings is attached wherein, by way of illustration and not limitation, the following is portrayed:

FIGS. 3A, 3B, 3C, 3D, 3E (3A longitudinal section, 3B transversal section, 3C detail of FIG. 3A, 3D section at A-A, 3E detail of FIG. 3B): A generator consisting of a plurality of bouquets of tubes for the ingress of second fluid (air) disgorging into various first fluid (water) ducts. FIG. 3A portrays bubbles of second fluid (air) in a duct, while FIG. 3B portrays bubbles in all the ducts. The section A-A of FIG. 3C illustrated in FIG. 3D portrays the section of the first extremities (61) of the tubes (6) of FIG. 3A. There is one duct for each bouquet, there being seven bouquets and seven ducts.

FIG. 4A portrays bubbles of second fluid (air) in a duct, while FIG. 4B portrays bubbles in all the ducts. There is one duct for each bouquet, there being forty-nine bouquets and forty-nine ducts.

FIGS. 5A, 5B (5A longitudinal section, 5B transversal section): A generator consisting of a plurality of bouquets of tubes for the ingress of second fluid (air) disgorging into various first fluid (water) ducts. FIG. 5A portrays bubbles of second fluid (air) in a duct, while FIG. 5B portrays bubbles in all the ducts. There are as many ducts as there are tubes, there being seven bouquets, forty-nine ducts and forty-nine tubes.

FIG. 9B, or the section at A-A of FIG. 9A portrays the transversal section of the first extremities (61) of the tubes (6).

Figure 1:
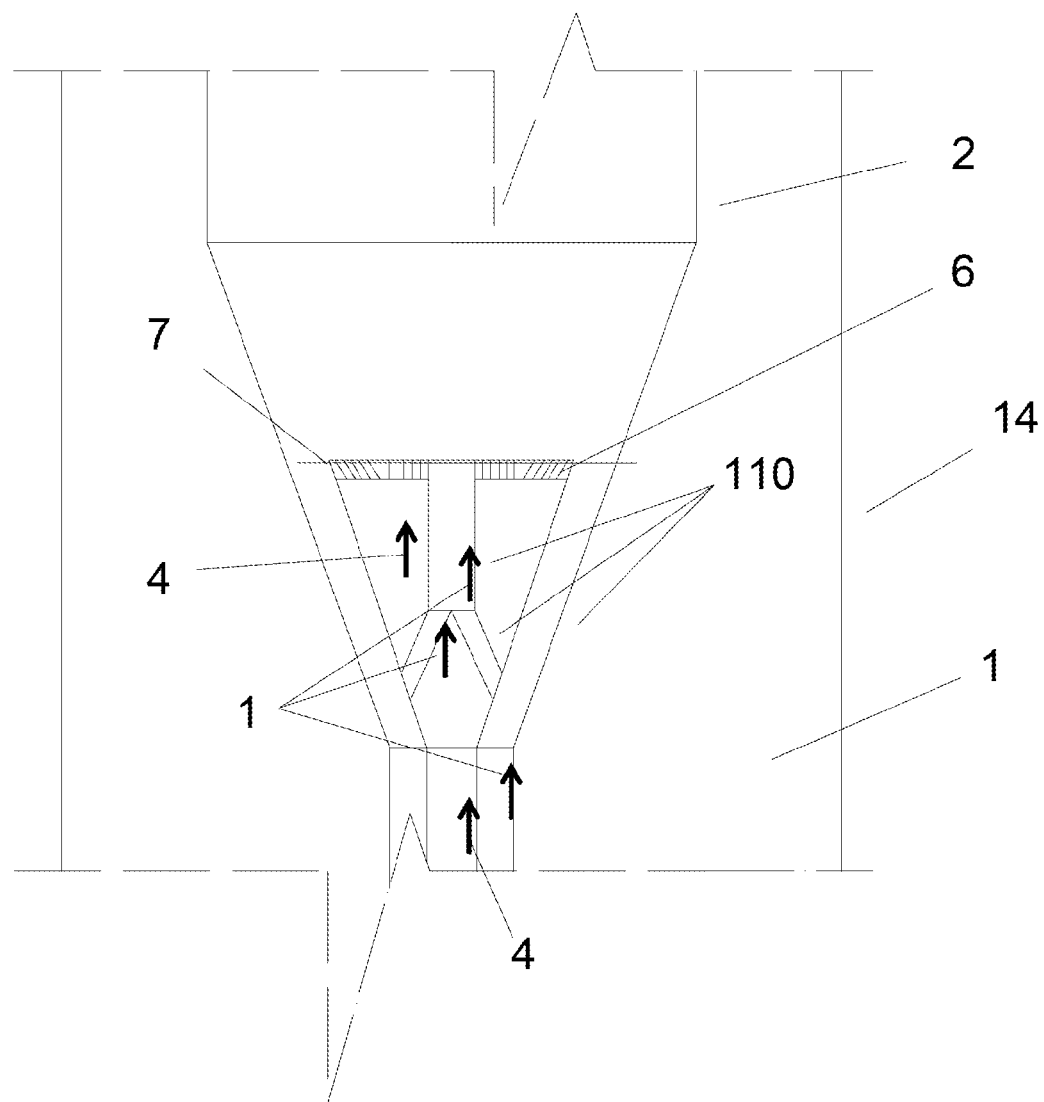
FIG. 1: A generator comprising a distributor for the ingress of second fluid, of lower density, which may be air, comprising a plurality of ducts of first fluid, of higher density, which may be water, to improve the distribution of bubbles of second fluid (air) in the first fluid (water).

The references shown in the figures correspond to the following items:
(1) First fluid, of a first density, this being a higher density, and which may be water
(2) Duct within the first fluid, which may be water
(3) Duct outlet
(4) Second fluid, of a second density, this being a lower density; a gaseous fluid which may be air, supplied at static and dynamic pressure
(5) Compressor
(51) Second fluid (may be compressed air) storage vessel
(6) Tubes (second fluid ingress tubes)
(61) First extremities of the tubes (6)
(62) Second extremities of the tubes (6)
(7) Inlet section for the ingress of the first fluid (which may be water) into the duct (directly or via the turbine)
(8) Turbine
(81) Turbine inlet
(9) Electrical generator
(10) Vane for directing the first fluid, which may be water
(14) Receptacle
(41) Drain
(42) Automatic filling device, by float level sensor
(106) Water collection tray
(107) Turbocharger
(108) Exhaust pipe
(109) Collection cone or funnel
(110) Channels for liquid at the second fluid (gaseous fluid or air) inlet
(111) Bubble of second fluid, which may be a gaseous fluid or air
(112) Elements to block the spaces between the bubbles (111) and the walls of the duct with liquid and bubbles of second fluid, which may be a gaseous fluid or air
($d_e$) Entry distance
($d_o$) Outlet distance
(P1) First depth
(P2) Second depth

PREFERRED EMBODIMENT OF THE INVENTION

Different forms of practical embodiments are shown below.

FIG. 1 portrays a conical- or diffuser-shaped second fluid (air) entry point as defined in the principal patent, comprising a plurality of channels (110) in order to achieve better bubble distribution and formation.

Figure 2:
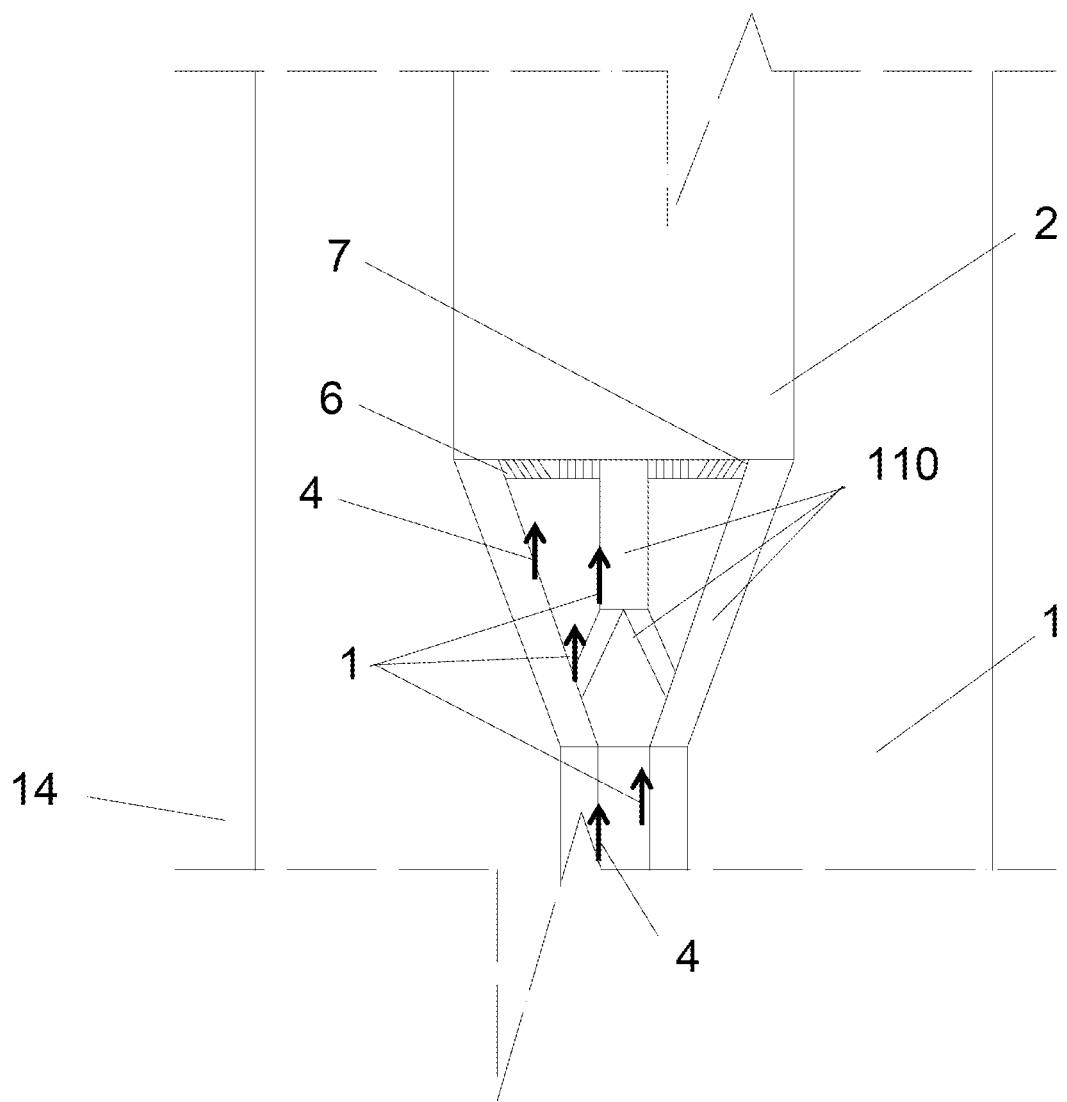
FIG. 2: A generator analogous to that portrayed in FIG. 1, where the duct of first fluid with bubbles of second fluid has a reduced profile.

FIG. 2 portrays a second fluid (air) entry point similar to that in FIG. 1 and with a reduced profile of the duct (2) for water with bubbles of the second fluid (air).

FIGS. 3A and 3B portray several bouquets of second fluid (air) entry tubes which disgorge into several first fluid (water) ducts, there being seven bouquets and seven ducts (2), each bouquet being connected to a duct (2). All the bouquets and ducts (2) are housed within the receptacle (14). The bubbles (111) of second fluid (air) have been portrayed as circumferences, both in the transversal section and the longitudinal section. The second fluid (air) entry points or second extremities (62) of the tubes (6) of the bouquet are of a smaller diameter than that of the bubbles (111) and are separated or have an outlet distance ($d_o$) between axes of symmetry which is approximately equal to the diameter of the bubbles (111). The size of the bubbles (111) depends fundamentally on the static and dynamic pressure and on the internal diameter of the tubes (6). The distance traveled by the second fluid within the tubes (6) or bouquets is approximately equal, in order that the load losses within the tubes (6) or bouquets are also approximately equal. It may be seen in FIG. 3C that the second extremities (62) of the central tubes (6) of each bouquet penetrate further into the ducts (2) so that the bubbles (111) may touch each other in accordance with a longitudinal axis of the duct (2). In other words:

12a) the second extremities (62) of the central tubes (6) of each bouquet penetrate a duct (2) up to a first depth (P1);
12b) the second extremities (62) of the peripheral tubes (6) of each bouquet penetrate a duct (2) up to a second depth (P2);
12c) the first depth (P1) is less than the second depth (P2).

The proportion of air that may be obtained, without blocking the spaces between the bubbles and the walls of the duct (2), is 51.8%; blocking these spaces, 66.6% is achieved; as there are seven spheres with radius r in a cylinder with radius 3r and a height of 2r (when blocking spaces, a volume of 4 pi $r^3$ should be subtracted from the 18 pi $r^3$ of the volume of the cylinder). FIG. 3D portrays a section at A-A in FIG. 3C. FIG. 3D is enhanced in detail in order to indicate the distance $d_e$.

Figure 4A:
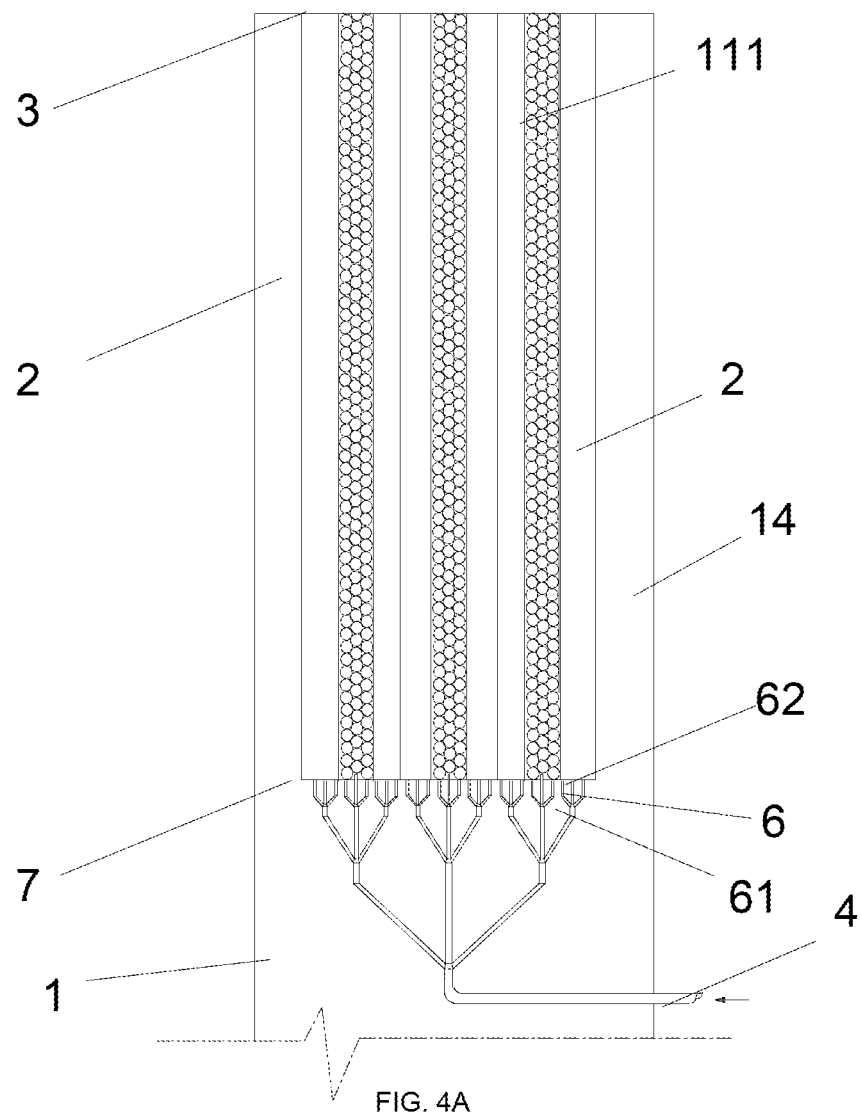
FIGS. 4A, 4B (4A longitudinal section, 4B transversal section): A generator consisting of a plurality of bouquets of tubes for the ingress of second fluid (air) disgorging into various first fluid (water) ducts.
Figure 4B:
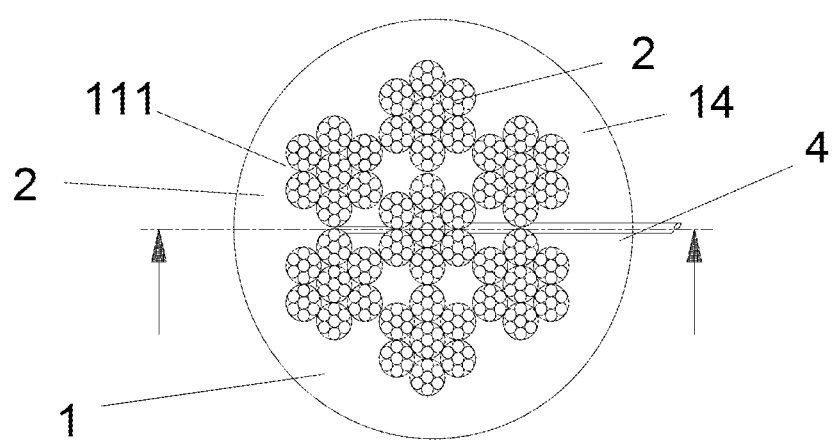

FIGS. 4A and 4B portray a system similar to that of FIGS. 3A and 3B, except that instead of seven bouquets, it comprises forty-nine bouquets, seven bouquets in each of the seven ducts (2).

FIGS. 5A and 5B portray several bouquets of second fluid (air) inlet tubes which disgorge into several first fluid (water) ducts (2), with seven bouquets, forty-nine ducts (2) and forty-nine tubes. All the bouquets and ducts are housed within the receptacle (14). The bubbles (111) of second fluid (air) have been portrayed as circumferences, both in the transversal section and the longitudinal section. The second fluid (air) entry points or second extremities (62) of the tubes (6) of the bouquet are of a smaller diameter than that of the bubbles (111) and are separated or have an outlet distance ($d_o$) between axes of symmetry which is approximately equal to the diameter of the bubbles (111). The size of the bubbles (111) depends fundamentally on the static and dynamic pressure and on the internal diameter of the tubes (6). The drawback of this system is the large number of tubes (6) and ducts (2) to be installed, one for each second fluid (air) inlet, but it enables the obtaining of elongated bubbles. The percentage of bubbles of second fluid, which may be a gaseous fluid or air, is 66.6%, representing a sphere with radius r versus a cylinder with radius r and a height of 2r. In this case, a single bubble occupies the transversal profile of each tube (2); for this reason there is only a single depth P=P1=P2 in each duct (2).

Figure 6:
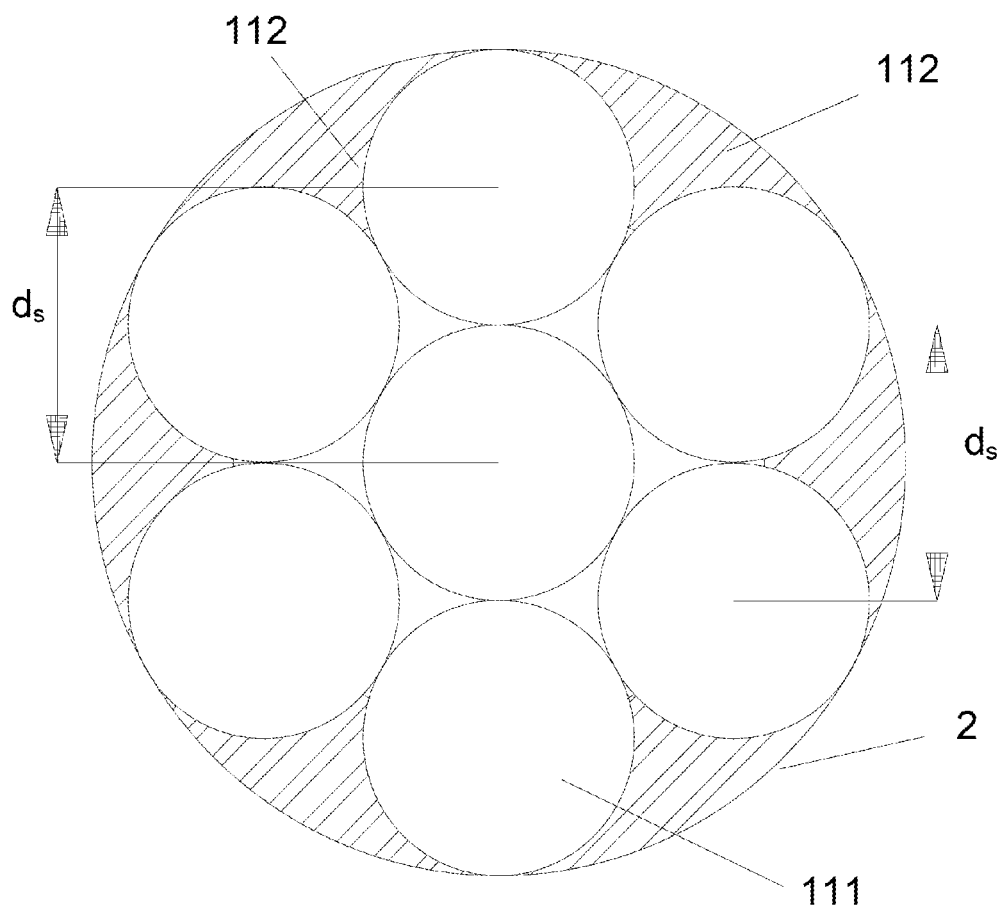
FIG. 6: Transversal section of a first fluid (water) duct with bubbles of second fluid (air) and with elements filling spaces or interstices.

FIG. 6 portrays a transversal section of a first fluid (water) duct with bubbles of second fluid (air), where the spaces between the bubbles (111) and the wall of the duct (2) have been blocked by means of elements (112) which prevent these spaces being filled with first fluid, this being a liquid fluid or water, and thus obtaining a higher proportion of second fluid (air) versus the first fluid (water), therefore increasing the efficiency of the Source of Renewable Energy.

Figure 7:
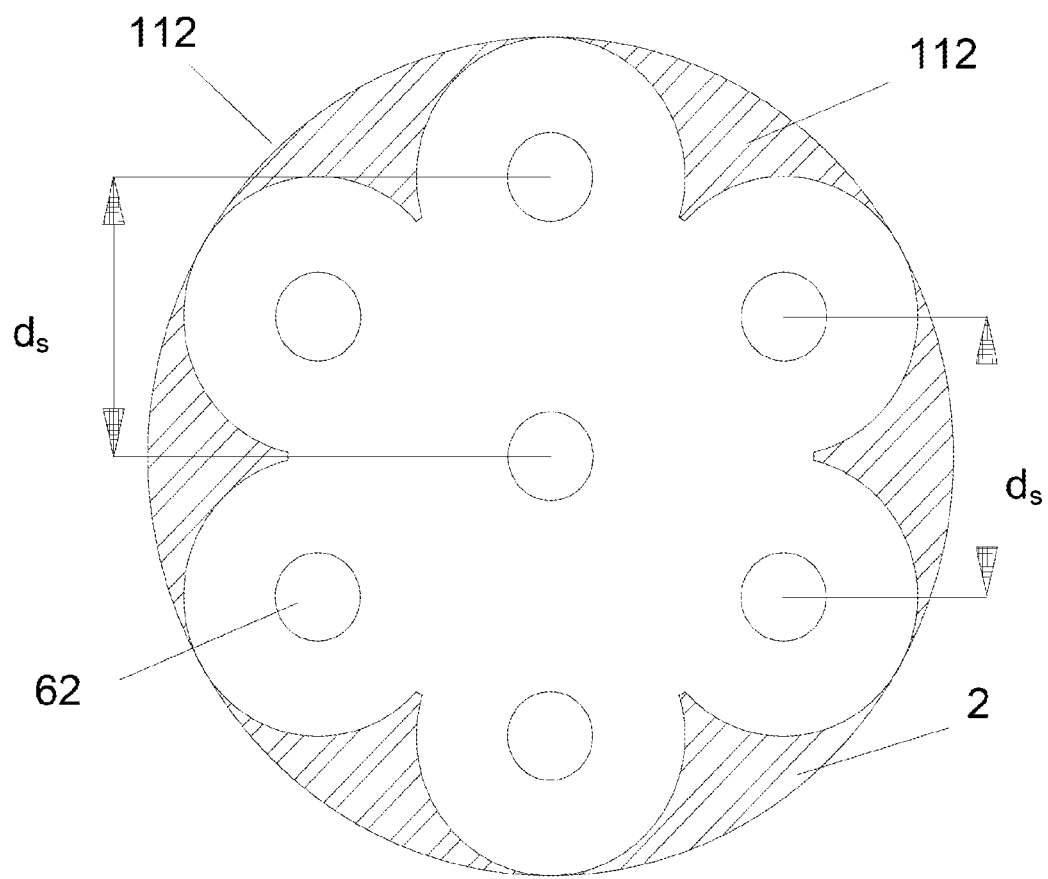
FIG. 7: Transversal section of a first fluid (water) duct with elements filling spaces or interstices, without portraying the bubbles.

FIG. 7 portrays the same example as FIG. 6 but without depicting the air bubbles (111). The outlet distances $d_o$, are greater than the diameter of the second extremities (62) of the inlet tubes (6), as the second fluid inlets into the duct (2) or second extremities (62) of the tubes (6) do not touch each other, but are some distance apart; in the case of adjacent tubes, this coincides with the diameter of the bubble (see FIG. 6). Conversely, the first extremities (61) of the inlet tubes (6) mutually touch, in a similar way to that portrayed in FIGS. 3D and 9B. This signifies that the distances ($d_e$) between adjacent tubes at the first extremities (61) are equal to the diameter of the tube.

Figure 8:
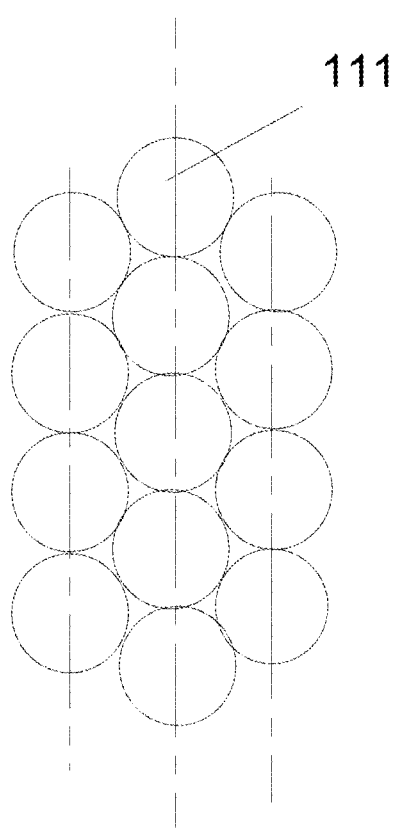
FIG. 8: Bubbles, aligned and touching each other.
Figure 9A:
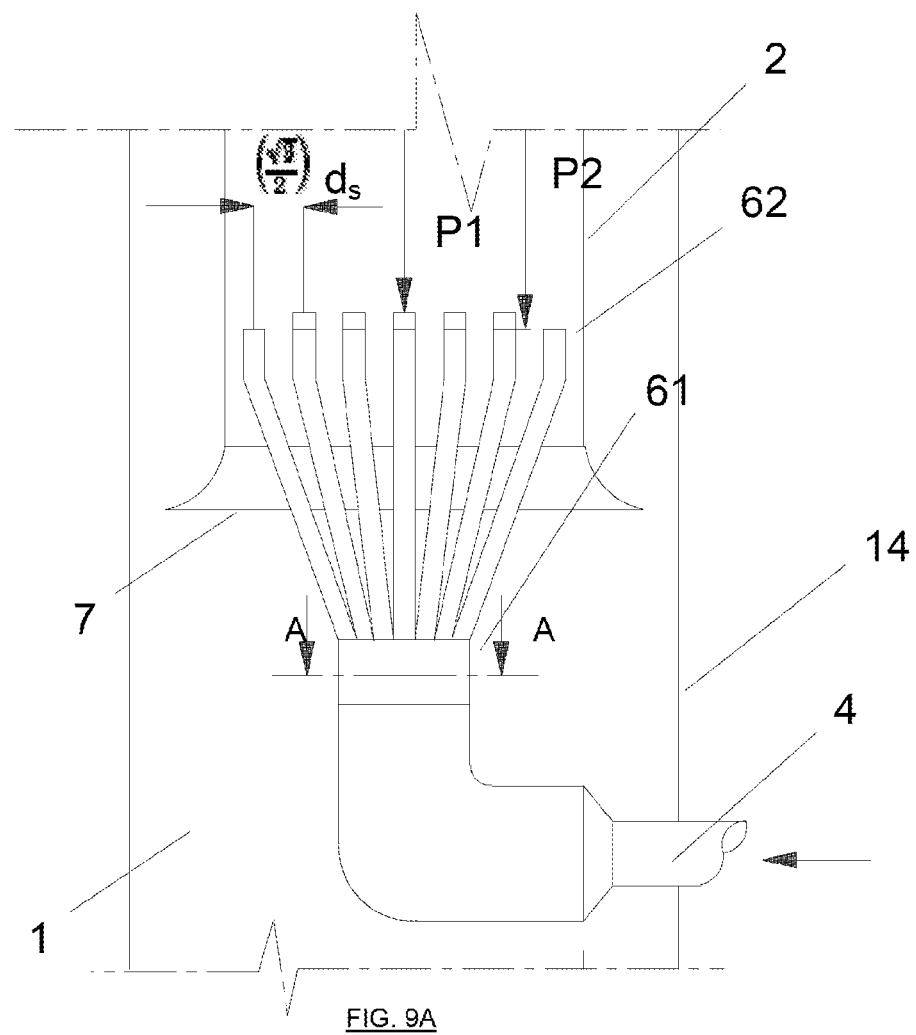
FIGS. 9A and 9B (9A longitudinal section, 9B section at A-A): Bouquet of tubes for the ingress of second fluid (air) disgorging into a single first fluid (water) duct. The duct features a hexagonal profile and the bouquet features thirty-seven tubes arranged in accordance with the hexagonal profile of the duct.
Figure 9B:
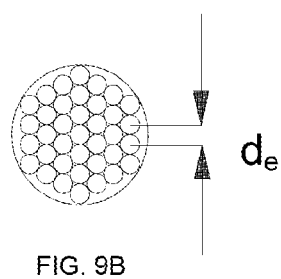

FIG. 8 portrays alignments of bubbles (111) touching each other. This arrangement is employed on both the longitudinal and transversal planes in order to obtain a greater proportion, or maximum volume, of second fluid (air) versus that of the first fluid (water). FIGS. 9A and 9B (9B: section at A-A) portray a bouquet of tubes (6) which disgorge into a single first fluid (water) duct (2) with a polygonal (hexagonal) profile. The level portrayed between the axes of symmetry of the outlet extremities (62) of the tubes (6) does not coincide exactly with the outlet distance $d_o$, but is equal to ($\sqrt{3}/2$) $d_o$, as it represents a projection of $d_o$, on the plane of the figure. This level and the exact distance $d_o$ are depicted in FIG. 11.

Figure 10:
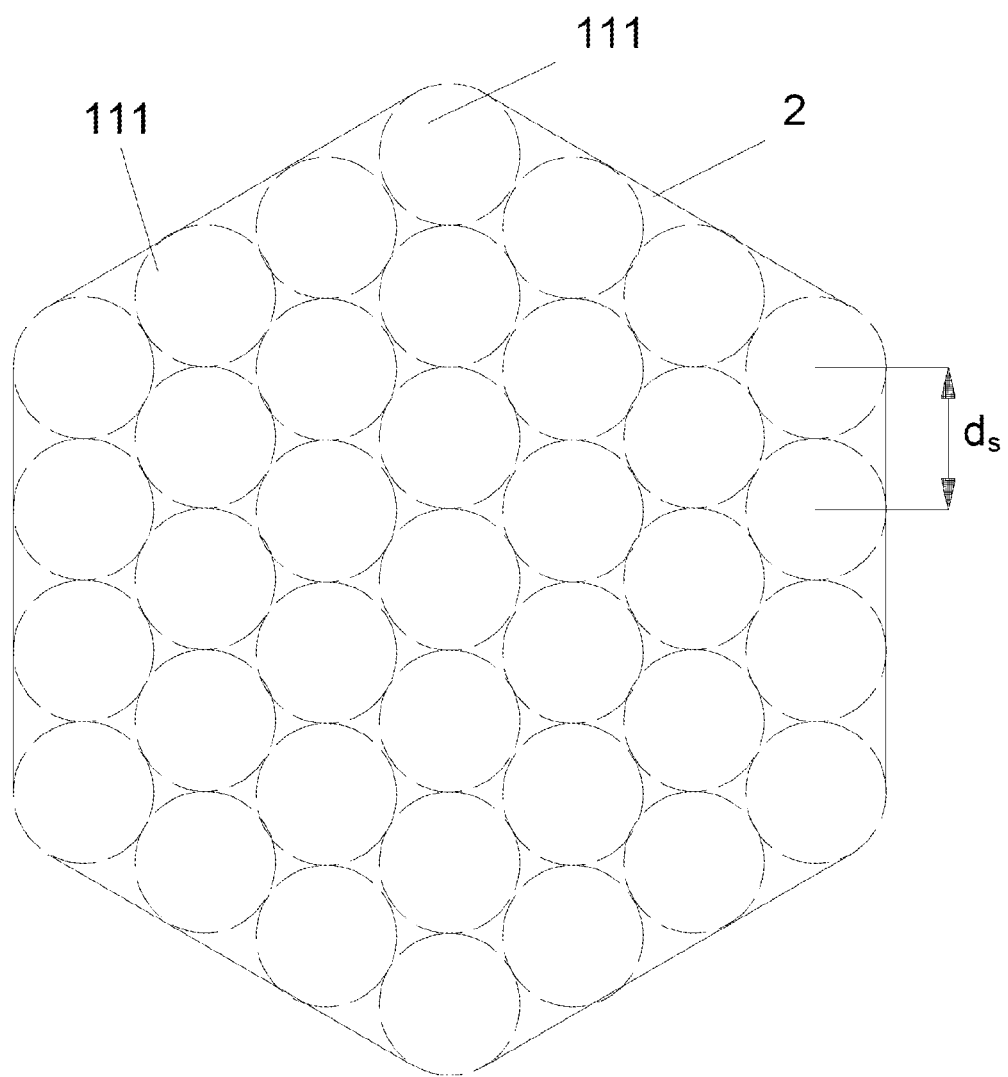
FIG. 10: Bubbles of the second fluid (air) in the first fluid (water) duct. The duct features a hexagonal profile.

FIG. 10 portrays the duct (2), featuring a hexagonal profile, and the arrangement of the bubbles, mutually touching, fitting into the profile of the duct (2).

Figure 11:
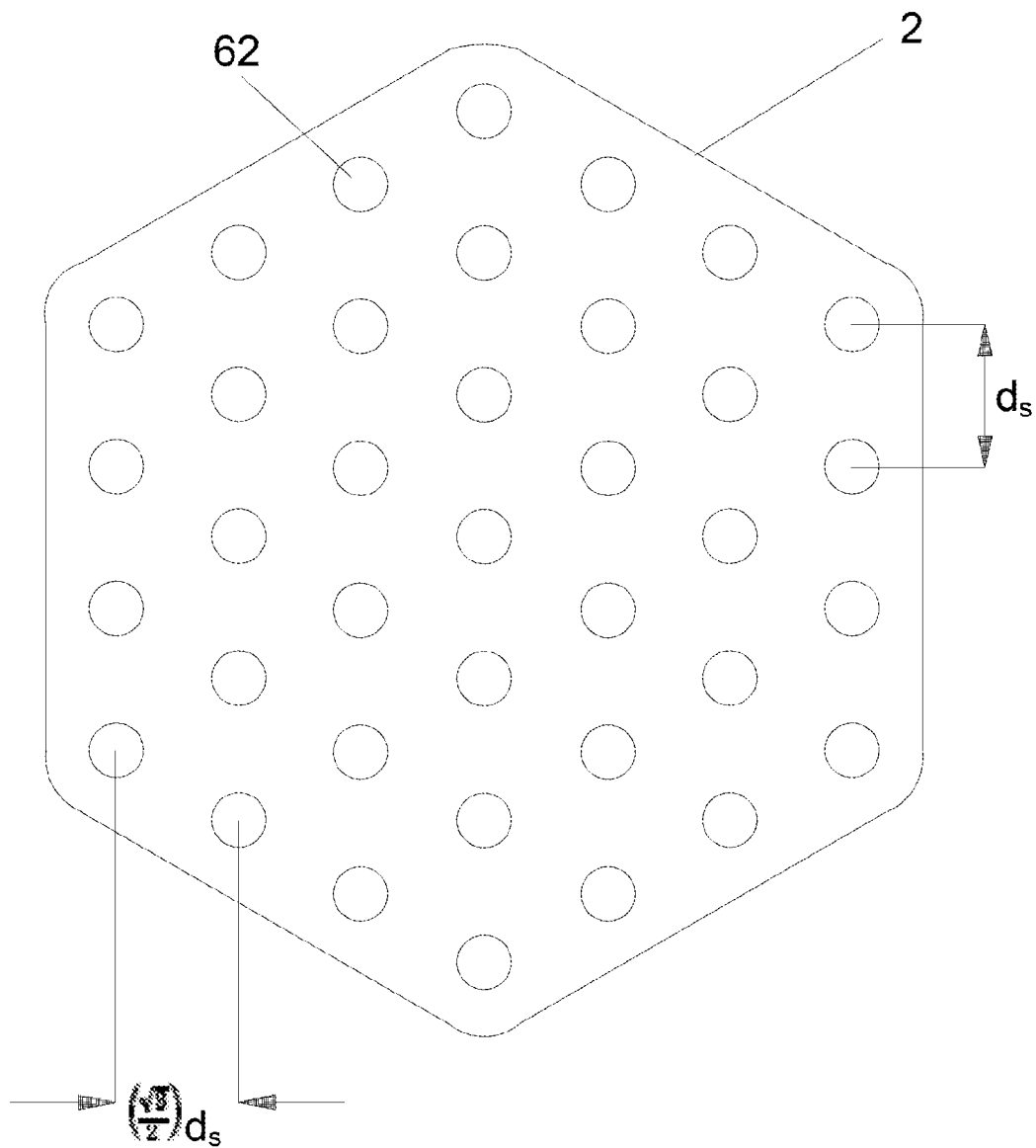
FIG. 11: Second fluid (air) inlets in the first fluid (water) duct, with a hexagonal profile. These generate the bubbles portrayed in FIG. 10.

FIG. 11 portrays the duct (2), featuring a hexagonal profile, and the arrangement of the second fluid (air) inlets into the duct (2) which give rise to the bubbles (111) portrayed in FIG. 10.

Figure 12:
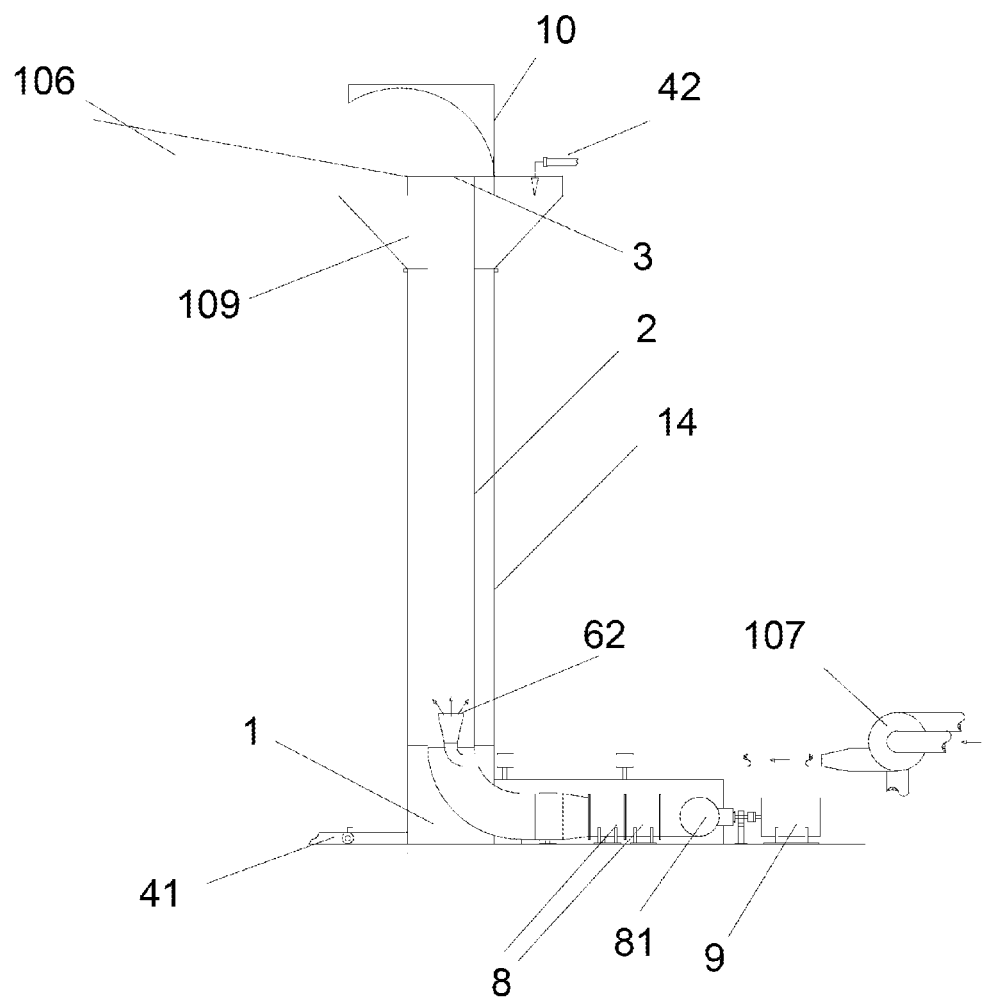
FIG. 12: Harnessing of exhaust gases by means of a turbocharger to produce compressed air to be used in the Source of Renewable Energy.

FIG. 12 portrays an application of the Source of Renewable Energy in which exhaust gases are harnessed for the production of compressed air by means of a turbocharger (107) which feeds the (statically and dynamically) compressed air into the duct (2) which initially contains water and subsequently contains water with air bubbles. This water with air bubbles rises through the duct (2) due to:

1. Archimedes' upthrust caused by the air bubbles.
2. The communicating-vessel effect between the interior of the duct (2) which contains water with air bubbles and the receptacle (14) which contains only water.
3. The air which enters under static and dynamic pressure.

When it reaches the summit it exits the duct (2) and is fed across the vane (10) which sends it to the separation tray (106); the air exits and the water descends down the receptacle (14). The flow of water is harnessed by the turbine (8) which produces electrical energy via the alternator (9). The water enters the turbine duct via the inlet (81).

The second fluid (air) inlet into the duct (2) is portrayed schematically. It represents any of the inlet systems depicted in FIG. 1 to 5, or 9.

Figure 13:
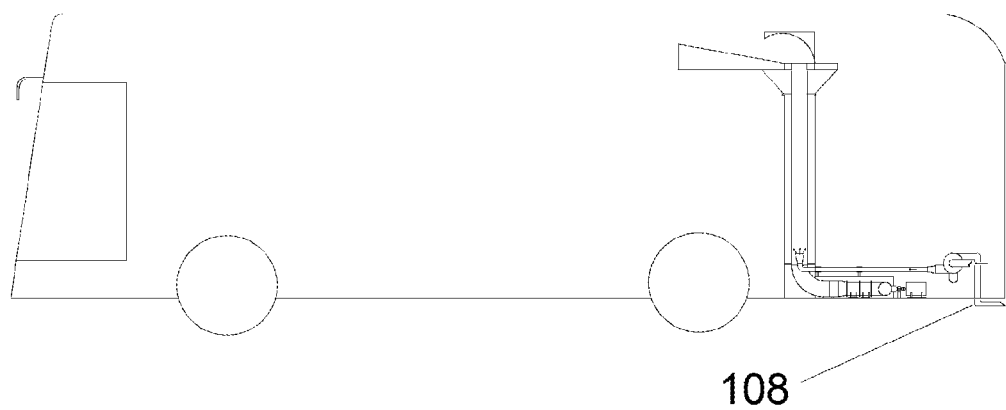
FIG. 13: Application of the system portrayed in FIG. 12 to a hybrid vehicle (bus).

FIG. 13 portrays the prototype depicted in FIG. 12 applied to a hybrid vehicle (bus).

Figure 14:
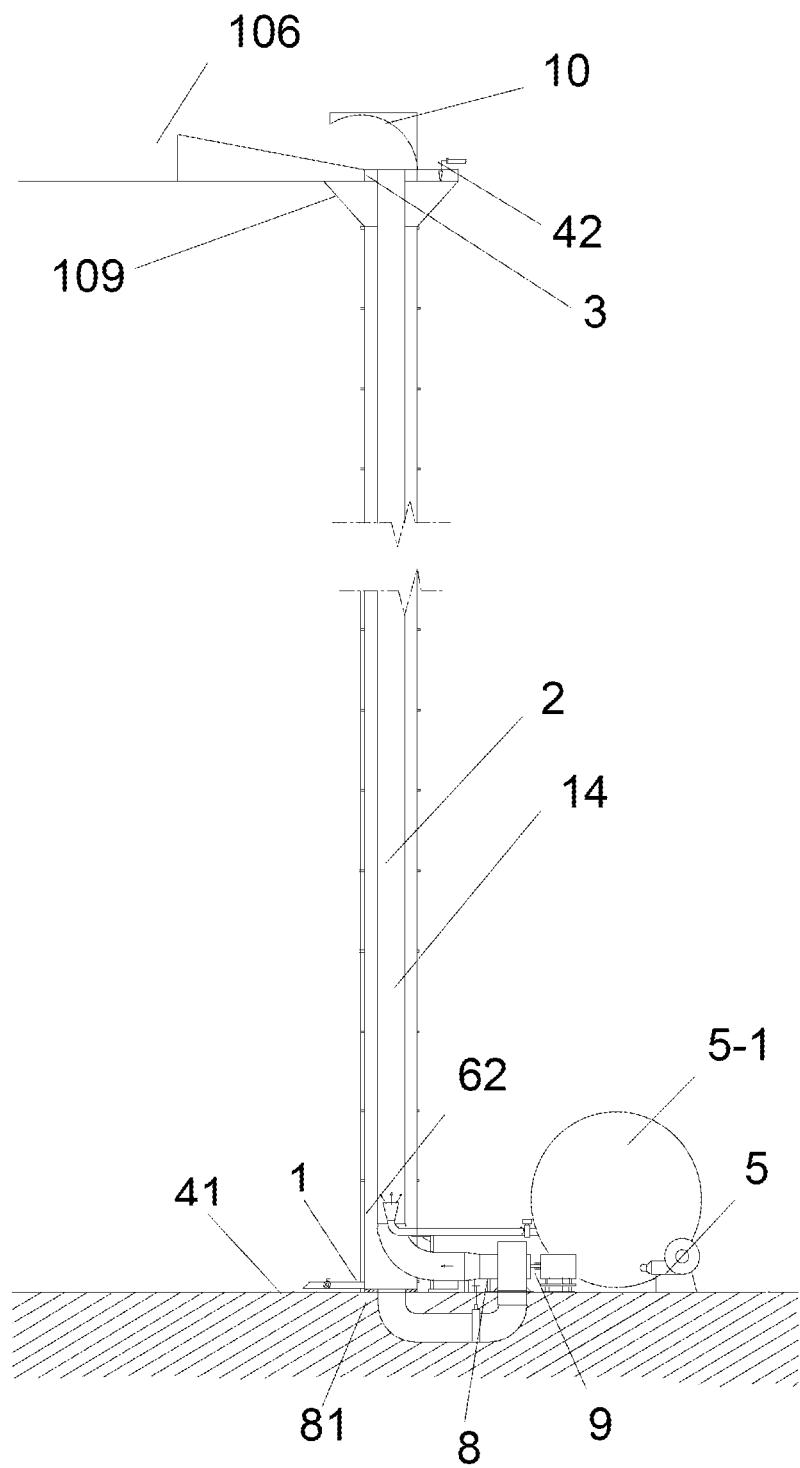
FIG. 14: Application of the Source of Renewable Energy installed on a patio wall or on the façade of a building.

FIG. 14 portrays a prototype in which the Source of Renewable Energy is stationary and features a great height, to be installed on a wall, to exploit the height of a patio or a façade.

In all else, operation is similar to that of FIG. 12, except that the air is produced or supplied by means of a mechanical compressor (5) and is stored in a vessel (51). As the compressor functions with electrical energy, an energy with a certain expense, it is necessary to achieve a high efficiency of the source, as otherwise it would not be profitable.

For this reason, the Source of Renewable Energy must be of a considerable height and the proportion of air in the duct (2) must be higher than that of water.

The second fluid (air) inlet into the duct (2) is portrayed schematically. It represents any of the inlet systems depicted in FIG. 1 to 5, or 9.

There may be variations, in respect of dimensions or shape, and details of a secondary nature, that do not modify the essence of the system described herein.

The invention claimed is:

1. A source which harnesses the difference in density between fluids for the production of renewable energy, where the source consists of:
   1a) a receptacle (14) which contains a first fluid (1) having a first density;
   1b) a supply (5, 51) of a second fluid (4) having a second density;
   1c) a duct (2):
      1c1) immersed in the first fluid (1);
      and which is comprised of:
      1c2) an inlet section (7);
      1c3) an outlet section (3);
   characterised in that it comprises:
   1d) a plurality of tubes (6) arranged in the form of a bouquet and configured so as to feed the second fluid (4) emanating from the supply (5, 51) into the inlet section (7).

2. A source which harnesses the difference in density between fluids for the production of renewable energy, as claimed in claim 1, characterised in that the tubes (6) are comprised of:
   2a) a first extremity (61) configured so as to receive the ingress of second fluid (4) emanating from a supply (5, 51);
   2b) a second extremity (62) configured so as to eject the second fluid (4) into the inlet section (7);
   where:
   2c) the first extremities (61) are separated from each other, at an entry distance ($d_e$) measured between the axes of symmetry of the tubes (6);
   2d) the second extremities (62) are separated from each other, at an outlet distance ($d_o$) measured between the axes of symmetry of the tubes (6).

3. A source which harnesses the difference in density between fluids for the production of renewable energy, as claimed in claim 2, characterised in that the outlet distance ($d_o$) is greater than the entry distance ($d_e$).

4. A source which harnesses the difference in density between fluids for the production of renewable energy, as claimed in claim 2, characterised in that the outlet distance ($d_o$) is equal to the diameter of the bubbles (111) of second fluid (4) within the first fluid (1).

5. A source which harnesses the difference in density between fluids for the production of renewable energy, as claimed in claim 2, characterised in that the source comprises:
   5a) a plurality of ducts (2);
   5b) a plurality of bouquets;
   where:
   5c) the second extremities (62) of a bouquet disgorge into the inlet section (7) of the same duct (2).

6. A source which harnesses the difference in density between fluids for the production of renewable energy, as claimed in claim 5, characterised in that each bouquet consists of seven tubes (6).

7. A source which harnesses the difference in density between fluids for the production of renewable energy, as claimed in claim 6, characterised in that the source consists of seven bouquets.

8. A source which harnesses the difference in density between fluids for the production of renewable energy, as claimed in claim 2, characterised in that the source comprises:
   8a) a plurality of ducts (2);
   8b) a plurality of bouquets;
   where:
   8c) each second extremity (62) of each bouquet disgorges into the inlet section (7) of a different duct (2).

9. A source which harnesses the difference in density between fluids for the production of renewable energy, as claimed in claim 2, characterised in that the source comprises a plurality of elements (112) to block the spaces between the second extremities (62) and a wall of the duct (2).

10. A source which harnesses the difference in density between fluids for the production of renewable energy, as claimed in claim 2, characterised in that the duct (2) features a polygonal transversal profile.

11. A source which harnesses the difference in density between fluids for the production of renewable energy, as claimed in claim 10, characterised in that the duct (2) features a hexagonal transversal profile.

12. A source which harnesses the difference in density between fluids for the production of renewable energy, as claimed in claim 10, characterised in that the bouquet consists of thirty-seven ducts (2).

13. A source which harnesses the difference in density between fluids for the production of renewable energy, as claimed in claim 2, characterised in that:
   13a) the second extremities (62) of the central tubes (6) of each bouquet penetrate a duct (2) up to a first depth (P1);
   13b) the second extremities (62) of the peripheral tubes (6) of each bouquet penetrate a duct (2) up to a second depth (P2);
   13c) the first depth (P1) is less than the second depth (P2).

14. A source which harnesses the difference in density between fluids for the production of renewable energy, as claimed in claim 1, characterised in that the source is comprised of:
   14a) a plurality of channels (110) configured so as to direct the first fluid (1) from the receptacle (14) to the inlet section (7).

* * * * *